(12) United States Patent
Fox et al.

(10) Patent No.: US 9,061,124 B2
(45) Date of Patent: Jun. 23, 2015

(54) HIGH-MODULUS SUPERELASTIC ALLOY WIRE FOR MEDICAL AND DENTAL PURPOSES

(71) Applicant: NeoMetrics, Inc., Plymouth, MN (US)

(72) Inventors: Karl Fox, Carver, MN (US); Jason Albers, St. Louis Park, MN (US); David Liebl, Eden Prairie, MN (US)

(73) Assignee: NeoMetrics, Inc., Plymouth, MN (US)

( * ) Notice: Subject to any disclaimer, the term of this patent is extended or adjusted under 35 U.S.C. 154(b) by 0 days.

(21) Appl. No.: 14/288,879

(22) Filed: May 28, 2014

(65) Prior Publication Data

US 2014/0370285 A1    Dec. 18, 2014

Related U.S. Application Data

(63) Continuation of application No. 12/550,954, filed on Aug. 31, 2009, now Pat. No. 8,801,633.

(51) Int. Cl.
*A61B 5/00*    (2006.01)
*A61M 25/09*   (2006.01)

(52) U.S. Cl.
CPC .................................. *A61M 25/09* (2013.01)

(58) Field of Classification Search
CPC .............................. A61M 25/01; A61M 25/09
USPC ............ 600/585; 623/1.15, 1.18, 1.19; 433/8, 433/16, 20–22
See application file for complete search history.

(56) References Cited

FOREIGN PATENT DOCUMENTS

| | | |
|---|---|---|
| JP | H04-292174 A | 10/1992 |
| JP | H09-508538 A | 9/1997 |
| JP | 2001-514544 A | 9/2001 |
| JP | 2005-131358 A | 5/2005 |
| JP | 2006-051386 A | 2/2006 |
| JP | 2006-246978 A | 9/2006 |

OTHER PUBLICATIONS

Office Action received for Japanese patent application 2012-527946, mailed Aug. 19, 2014, 8 pages.

*Primary Examiner* — Max Hindenburg
(74) *Attorney, Agent, or Firm* — Fredrikson & Byron, P.A.

(57) ABSTRACT

A wire used in the medical field for guiding purposes, as well as in other fields, such as in the field of orthodontics for teeth aligning purposes. The wire, when prepared for use in such applications, exhibits an innovative blend of advantageous properties, including enhanced kink resistance over stainless steel wires and enhanced stiffness over Nitinol wires, which enhance its use as a medical guidewire or stylet, and further, as an arch wire in orthodontia applications.

37 Claims, 2 Drawing Sheets

HIGH-MODULUS SUPERELASTIC ALLOY WIRE FOR MEDICAL AND DENTAL PURPOSES

RELATED APPLICATIONS

This application is a continuation of and claims priority to U.S. application Ser. No. 12/550,954 filed Aug. 31, 2009, the contents of which are incorporated herein by reference.

BACKGROUND

1. Field of the Invention

The present invention relates to the field of medical and dental devices, and more particularly to guidewires and stylets used in intra-vascular procedures and arch wires used in orthodontia procedures.

2. Description of the Related Prior Art

A major requirement for medical guidewires and other guiding members, whether they are formed of solid wire or tubular members, is that they have sufficient column strength and stiffness to be pushed through passageways in a patient, such as the patient's vascular system, with minimal kinking or binding. However, the distal section of the guidewire must also be flexible enough to avoid damaging the blood vessel or other body lumen through which it is advanced. Accordingly, efforts have been made to provide guidewires having a favorable combination of both strength and flexibility in order to make them suitable for their intended uses. However, strength for pushing and flexibility for turning without damaging vascular walls tend to be diametrically opposed to one another, such that an increase in one usually involves a decrease in the other, as exemplified below.

The cores of conventional guidewires have been made of many different materials. Two of the more popular materials are stainless steel and Nitinol. In particular, stainless steel has good pushability properties as well as good torque qualities. In turn, guidewire cores formed of such material are generally found suitable for being advanced, and further, for being rotated, so as aid in their being maneuvered, through a patient's vascular system. However, such steel core guidewires tend to be stiff, i.e., not easily bent, and limited in their flexibility. Therefore, the steel guidewire can be found to bind or kink as it is advanced in the vascular anatomy. As is known, once the guidewire is kinked, it must often be discarded and replaced with a new guidewire.

On the other hand, guidewires formed with Nitinol cores are found to have the flexibility that is warranted for negotiation through a tortuous path in a patient's body lumens or vessels. In turn, when being advanced through a patient's vascular system, such guidewires are found to exhibit lower potential for either damaging the patient's vessel/body lumen or kinking/binding. Unfortunately, such Nitinol guidewires are found to be quite soft while exhibiting good shape memory. Accordingly, they are found to have limited pushability against resistance of tortuosity (e.g., in comparison to guidewires having stainless steel cores) because they tend to straighten out or return to their original shape during their advancement. The shape memory can make it difficult for a physician to shape the tip of the guidewire with his fingers for accessing difficult to reach portions of the patient's vascular system.

In light of the above, efforts have been made to blend the favorable characteristics of both stainless steel and Nitinol in guidewires. These efforts have resulted in a variety of differing designs. One widespread wire design involves joining materials of differing properties along the wire's extent. As shown, three materials are sequentially joined in forming the core of the wire: (i) stainless steel used as a proximal portion, (ii) a segment of binary superelastic alloy distally joined to the stainless steel portion (an alloy often utilized is Nitinol), and (iii) a further segment of stainless steel distally joined to the superelastic segment, forming the end of the wire. Due to its stiffness, the proximal portion of stainless steel allows the wire to be pushable over much of its length as it is threaded invivo. However, because the superelastic segment exhibits good kink resistance, it aids the movement of the wire's distal region through the tortuosity of the system in which the wire is being threaded. Finally, the distal stainless steel segment, serving as a shaping ribbon, enables adequate control and shapeability of the wire at its distal end.

However, there are drawbacks to such wire core configurations. First, extreme care and precision are required in joining distinct sections in forming the wire core, which lends itself to significant manufacturing time and cost. Second, potential joint failures along the length of the core represent an ever-present risk during use of the wire. Third, while the use of stainless steel and superelastic materials in the wire core help to exhibit both column strength and kink resistance, respectively, one or more of these properties can generally be found to be impeded when joining separate materials.

Similar to that described above concerning guidewires in the medical field, there are other fields of art that would be well served with wires having a combination of both column strength and kink resistance properties. One example is in the field of dentistry, specifically with respect to arch wires used for orthodontia. Such arch wires need sufficient column strength and stiffness for their use in effectively aligning or straightening teeth, with minimal kinking or binding to the wires. To this end, the arch wires must be flexible enough so as to be routinely reshaped by a dentist as a patient's teeth are aligned over time. Standard binary Nitinol has generally been used as the material of choice for such arch wires because of its good flexibility properties; however, such material is generally lacking in terms of its overall strength and stiffness properties.

What are needed are apparatus and/or systematic methods to address or overcome one or more of the limitations briefly described above with respect to conventional medical wires used for guiding purposes, and which may be further applicable in other fields where such combined wire properties would be considered advantageous, such as with orthodontia wires used for teeth aligning purposes.

SUMMARY OF THE INVENTION

Embodiments of the invention provide a wire used in the medical field for guiding purposes, as well as in other fields, such as in the field of orthodontics for teeth aligning purposes. The wire, when prepared for use in such applications, exhibits an innovative blend of advantageous properties, including enhanced kink resistance over stainless steel wires and enhanced column stiffness over Nitinol wires, which enhance its use as a medical guidewire or stylet, and further, as an arch wire in orthodontia applications.

In one embodiment, a wire is provided for use for one of medical or orthodontia purposes. The wire comprises an elongated, flexible metal wire core at least partially formed of a high-modulus superelastic alloy. The alloy exhibits both an upper plateau (UP) and a lower plateau (LP) from a 3-point bend test that are respectively greater than a UP and a LP from same 3-point bend test of binary Nitinol alloy with substantially similar diameter as the wire core.

In another embodiment, a wire is provided for use for one of medical or orthodontia purposes. The wire comprises an elongated, flexible metal wire core at least partially formed of a high-modulus superelastic alloy. The alloy has both an upper plateau (UP) and a lower plateau (LP) from a 3-point bend test that are respectively greater than a UP and a LP from same 3-point bend test of binary Nitinol alloy with substantially similar diameter as the wire core. The high-modulus superelastic alloy comprises a trinary alloy consisting of Nickel, Titanium, and Cobalt In an additional embodiment, a wire is provided for use for one of medical or orthodontia purposes. The wire comprises an elongated, flexible metal wire core solely formed of a high-modulus superelastic alloy. The alloy has both an upper plateau (UP) and a lower plateau (LP) from a 3-point bend test that are respectively greater than a UP and a LP from same 3-point bend test of binary Nitinol alloy with substantially similar diameter as the wire core. The wire core comprises a single continuous body.

In a further embodiment, a wire is provided for use for one of medical or orthodontia purposes. The wire comprises an elongated, flexible metal wire core solely formed of a high-modulus superelastic alloy. The alloy has both an upper plateau (UP) and a lower plateau (LP) from a 3-point bend test that are respectively greater than a UP and a LP from same 3-point bend test of binary Nitinol alloy with substantially similar diameter as the wire core. The high-modulus superelastic alloy comprises a trinary alloy consisting of Nickel, Titanium, and Cobalt. The wire core comprises a single continuous body.

DETAILED DESCRIPTION

Figure 1:
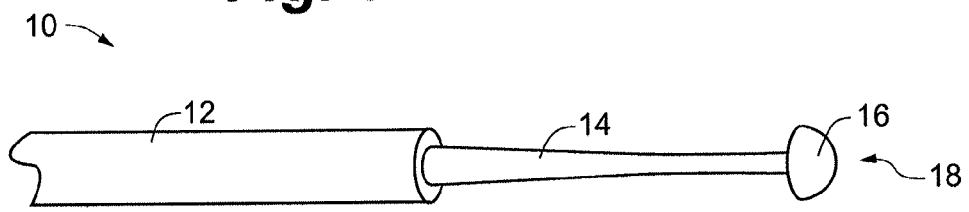
FIG. 1 is a side view of an exemplary wire core of a guidewire in accordance with certain embodiments of the invention.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

In the medical field, wires used for guiding purposes are employed in a wide variety of procedures. For example, as described above, guidewires are typically used to facilitate the intravascular placement of medical devices, such as catheters and other devices, inside a patient's body. Conversely, in the field of dentistry, particularly relating to orthodontia, arch wires are employed for aligning teeth. The prepared wires described herein are equally applicable in each of these fields, and while guidewires and arch wires are the corresponding devices described herein utilizing such configured wires, such is done solely for exemplary purposes. To that end, the embodied wires of the invention are applicable to any field in which a wire having properties of column strength and stiffness with minimal kinking or binding is applicable.

As described above, a primary consideration in designing medical wires for guiding purposes involves determining how best to achieve a sufficient combination of column strength and kink resistance. A variety of efforts have been put forth to achieve such a combination; however, such efforts have generally resulted in limited success. For example, locating a guidewire core material that exhibits such a combination of properties has been difficult. Similarly, decreasing the core profile of a guidewire to achieve such a combination of properties has generally been unsuccessful, as the resulting cores have been found to exhibit general loss in pushability. One approach that has resulted in some success involves using a wire coil at the distal end of the guidewire. However, even with this design, limitations have also been encountered due to potential wear of the linkage between the coil ends and the wire core during the wire's use.

Certain embodiments of the invention provide wires used for guiding purposes that have constructions which overcome one or more of the above-described limitations of conventional wires. In particular, the wires embodied herein provide an innovative blend of favorable properties, including enhanced pushability and flexibility, as well as having other construction characteristics/properties which make them advantageous over other commercially available wires.

FIG. 1 illustrates an exemplary wire core 10 of a guidewire in accordance with certain embodiments of the invention. As shown, the wire core 10 has an elongated, solid member. In certain embodiments, such core 10 has a generally round cross section; however, the invention should not be limited to such. For example, while not shown, the core 10, instead of having a round cross-section, can have one or more flat outer surfaces. As should be appreciated, the core 10 can be any desirable length, and is accordingly sized based on the procedure(s) in which the guidewire is intended. For example, in certain embodiments, the core 10 can be sized to be greater than about one meter in length in order to be advanced through a corresponding length of a patient's body lumens or vessels (not shown), e.g., in the patient's vascular system. It should be appreciated that the sizing of the wire core 10 can be varied as desired, such that the length of the core 10 is greater than one meter. For example, in certain embodiments, the length of the core 10 may be sized to have a length of at least 4.5 meters.

As illustrated, the core 10 includes a proximal section 12 having a generally uniform diameter and a distal section 14 having a generally varying diameter. In certain embodiments, the distal section 14 includes an expanded portion 16 at its distal end 18. Generally, the distal end 18 is initially shaped to be compact (e.g., resembling a rectangular block or any other desirable shape) and then modified to form an expanded portion.

While not shown, in certain embodiments, an additional element for a guidewire can be a wire coil; however, the invention should not be limited to such. As alluded to above, such wire coil is combined with the wire core 10 so as to surround the core distal section 14 to add column strength to the section 14, particularly in cases where the distal section 14 of the wire core 12 is formed of a superelastic material. With use of a wire coil, in certain embodiments, another element for a guidewire can be a bonding agent, used to adhere end portions of the wire coil to the wire core 12. Further description of such guidewire elements is found in application, U.S. Ser. No. 11/735,289, entitled "Medical Guidewire," the teachings of which are hereby incorporated by reference. While embodiments described therein involve certain embodiments concerning medical guidewires, among other devices, its general teachings concerning the wire coil and bonding agent can be applicable herein as well; however, the invention should not be limited to such. Instead, it should be appreciated that variations of one or more of the coil and bonding agent can be used, or alternatively, one or more of such elements may not be used with the wire core 10 at all.

Also, while not shown, in certain embodiments, another further element for the guidewire can be a coating of material added to overlay a portion of the core 10. Such coating material is generally added to the core 10 to enhance its lubricity to reduce the friction between the guidewire and the patient's vascular anatomy during the wire's advancement there through. In certain embodiments, the coating material is a hydrophilic coating, such as Polyvinylpyrrolidone (PVP) or a lubricious coating such as polytetrafluoroethylene (PTFE) or the like. As would be appreciated by those skilled in the art, the extent of the core 10 over which the coating is added is variable depending on the wire's designed functioning. For example, in certain embodiments, such coating material is used to coat at least the distal end 18 of the core 10; however, the invention should not be limited to such. Instead, it should be appreciated that other embodiments can involve the coating material being used to coat at least the distal section 14 of the core 10, and in further embodiments, the coating material can be used to coat the entire extent of the core 10. Alternatively or additionally, in certain embodiments, when a wire coil is used to surround the core distal section 14, the coating material can be used to coat the wire coil as well.

While not shown, it should be appreciated that an arch wire for orthodontia applications is more of a simplified version of the wire core 10 of FIG. 1. In particular, because arch wires are utilized for aligning teeth (often requiring the arch wire to be typically a single uniform diameter over its extent), it does not share the same shaping and length constraints that apply to guidewires. Accordingly, the skilled artisan would understand the respective configuration of an arch wire through examination of the wire core 10 depicted in FIG. 1 for an exemplary guidewire of the invention.

The embodied wire core 10 for both a guidewire and an arch wire is at least partially formed of a high-modulus superelastic alloy. The alloy is formed of a Nickel Titanium Cobalt trinary alloy, which is commercially available from SAES Smart Materials, Inc, principally located in New Hartford, N.Y., U.S.A. The applicants have found that when the alloy is prepared for utilization in guidewire/arch wire applications, the wire exhibits an innovative blend of advantageous properties, including enhanced kink resistance over stainless steel wires and enhanced stiffness over typical binary superelastic alloys, such as binary Nitinol alloy wires. One configuration of this alloy can involve it being principally formed of Nickel (approximately 55.3% in weight) and Titanium (approximately 43.4% in weight), with Cobalt being a lesser additive (approximately 1.3% in weight); however, these weight distributions can be modified as desired. In certain embodiments, the trinary alloy has a weight percentage of Cobalt less than or equal to 2% and weight percentages of Nickel and of Titanium greater than 40%.

In preparing the wire of the invention for its utilization in guidewire/arch wire applications, a high temperature treatment straightening process is performed. The general parameters for one such process can involve heating in a temperature range of 450° C. to 600° C. for a period of time of 30 seconds to 150 seconds. As should be understood, these parameters will vary based on size and composition of the wire, as well as the forming apparatus used to straighten the wire. In addition, torsion may be applied during the heating process, again depending on the parameters of the wire. As would be appreciated by those skilled in the art, a wide variety of high temperature techniques and/or processes are currently known that can be used for straightening guidewires/arch wires. Therefore, while the general parameters of only one such technique/process have been provided, the invention should not be limited to such. Instead, any of the variety of other known high temperature techniques and/or processes can be likewise used for straightening the wire embodied herein and continue to fall within the spirit of the invention.

Figure 2:
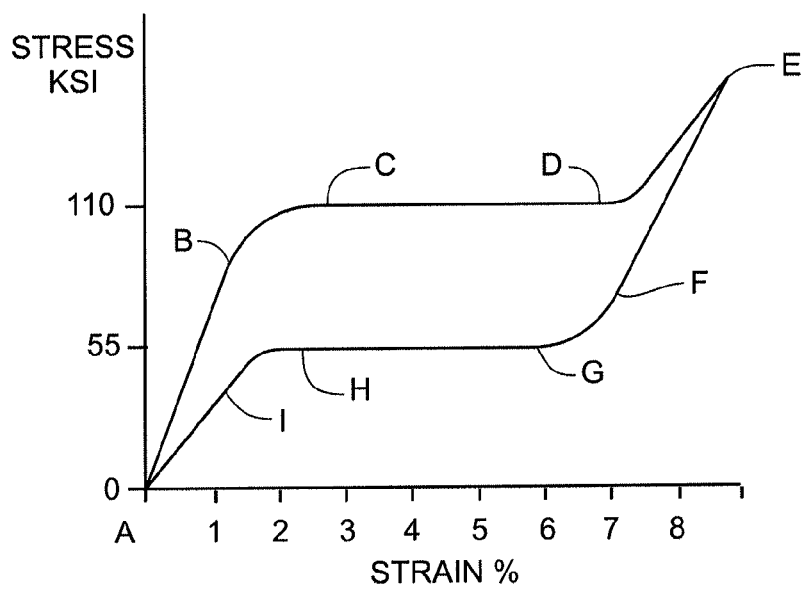
FIG. 2 is a schematic, graphical illustration of stress-strain relationship of superelastic material.

FIG. 2 illustrates an idealized stress-strain relationship plot for an alloy material having superelastic properties, such as Nitinol, generated upon tensile testing of the material. In brief, the curve shows the material's change from its original shape to an austenite phase (at which the specimen exhibits a relatively high tensile strength) to a martensite phase (at which the specimen exhibits a relatively low tensile strength) and back again to the material's original shape.

As shown, the line from point A to point B on the plot represents the initial elastic deformation of the specimen. After point B, the strain or deformation is no longer proportional to the applied stress and between point B and point C, the material starts to undergo stress-induced transformation from its austenite phase to its martensite phase. To this end, at point C, the material enters a region of relatively constant stress with significant deformation or strain. It is in the region of Point C to point D that the transformation from austenite to martensite occurs. At point D, the stress-induced transformation to the martensite phase is substantially complete. Beyond point D, the stress-induced martensite phase begins to deform, elastically at first, but, beyond point E, the deformation is plastic or permanent. If plastic deformation occurs, the strain will not return to zero upon the removal of the stress.

When the stress applied to the superelastic alloy material is removed, the material recovers to its original shape, provided that there was no permanent deformation to the martensite phase. At point F in the recovery process, the material begins to transform from the stress-induced, unstable martensite phase back to the more stable austenite phase. In the region from point G to point H, which is also an essentially constant stress region, the phase transformation from martensite back to austenite is essentially complete. The line from point I to the starting point represents the elastic recovery of the metal to its original shape.

Figure 3:
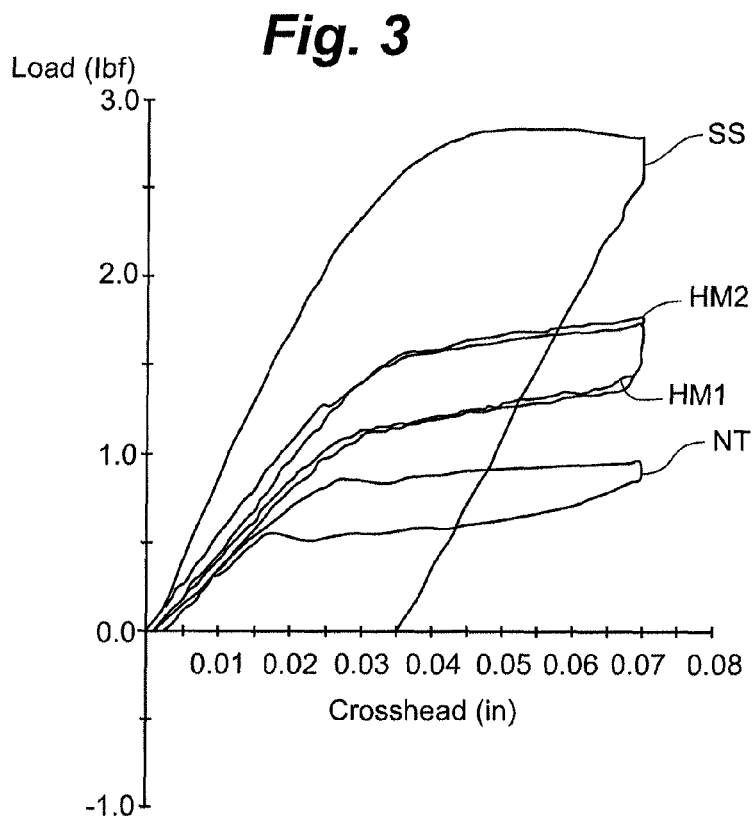
FIG. 3 is a graphical illustration of stress-strain relationship of the high-modulus superelastic alloy wire of the invention (before and after accelerated aging) as compared to stainless steel wire and binary Nitinol alloy wire.

By way of comparison, FIG. 3 depicts stress-strain relationship graph of stainless steel wire (304 stainless steel) referenced as line SS, the high-modulus superelastic alloy wire of the invention (both before and after accelerated aging) referenced as lines HM1 and HM2, respectively, and binary Nitinol alloy wire referenced as line NT, from 3-bend tests performed on the differing materials. Regarding the wire sizes of the specimens, all have substantially similar diameters. With respect to the accelerated aging of the wire of the invention, the wire was aged at 75° C. for approximately 110 hours to represent a six-month shelf life.

3-point bend testing is well known in the industry for determining superelastic characteristics of guidewire materials. In particular, the test involves a guidewire segment being placed on a certain rigid material having a gap of certain length therein, wherein a section of the guidewire is positioned to overlay the gap with the opposing ends of the guidewire section being supported such that the guidewire section extends taut across the gap length. In turn, a vertical force (e.g., a load) is placed on the wire section that overlays the gap. Depending on the variation of the 3-point bend test being performed, the vertical force is positioned at one or more points on the wire section overlaying the gap length. For example, in one variation of the test, the vertical force is positioned at a midpoint of the wire section overlaying the gap length. In such case, upon subjecting the wire to the load at the midpoint, the wire is found to deflect from its straightened orientation, and after the load is removed, the wire material is generally found to exhibit its recovery characteristics.

In certain embodiments, the 3-point bend test performed on each of the guidewire specimens of FIG. 3 involved a midpoint load being applied to the guidewire section overlaying the gap length. The gap length equaled 20 times the diameter of the wire and the load was applied such that a deflection of at least 4 times the diameter of the wire was measured. The resulting stress-strain behavior of the guidewires was accordingly plotted, as provided in FIG. 3.

As was expected, the 304 stainless steel wire exhibited higher column strength and stiffness (tolerance for stress via the exerted load) than either of the high-modulus superelastic alloy wire of the invention or the binary Nitinol alloy wire; however, the steel lacked any recovery mechanism, i.e., being unable to revert back to its original shape. Accordingly, in applying an increasing amount of stress on the steel wire (peak load level of approximately 2.8 lbf), the wire's deflection was observed to generally plateau before the material eventually gave way, leaving the wire with a significant permanent deflection. By way of comparison, the binary Nitinol alloy wire showed far lower column strength and stiffness (peak load level of approximately 0.9 lbf) than the 304 stainless steel material, but as expected, the Nitinol alloy recovered to its original shape via transition back to its austentite phase. Thus, its superelastic properties enabled the Nitinol alloy to revert in this fashion without any significant permanent deflection.

With further reference to FIG. 3, each of the high-modulus superelastic alloy wire specimens of the invention (before and after accelerated aging) exhibited advantageous characteristics of each of the 304 stainless steel and binary Nitinol alloy wires. As shown, the wire of the invention exhibited higher column strength and stiffness (peak load level of approximately 1.7 lbf) than the binary Nitinol alloy wire, while being able to recover back to its original shape via transition back to its austentite phase. Accordingly, the wire of the invention is found to exhibit a good blend of properties of the 304 stainless steel and binary Nitinol alloy wires that are favorable for guidewire and arch wire applications, i.e., enhanced kink resistance over stainless steel wire and enhanced column stiffness over Nitinol wire. To that end, by its superelastic recovery mechanism, the wire of the invention, even when aged, can recover to its original shape following stress-related deflection.

It should be appreciated that the plots of FIG. 3 is just one comparison of an exemplary wire configuration of the invention with stainless steel and binary Nitinol alloy wires. In their tests, applicants have discovered that the divergence of properties of the wire of the invention shared with stainless steel and Nitinol can be varied over a wide spectrum through variance of the characteristics (such as size and weight components of the alloy, thermal processing parameters of the straightening process, etc.) of the wire of the invention. For example, while FIG. 3 shows the 3-point bend Upper Plateau (UP) of the wire of the invention could be made to be approximately 65% of the peak 3-point bend value of 304 stainless steel wire, in certain embodiments, the range of variance can be from approximately 45% to approximately 75%. Thus, in certain embodiments, when desiring a high column strength value in the center of such range, the 3-point bend UP of the wire of the invention can be configured to be approximately 60% of the peak 3-point bend value of 304 stainless steel wire. When designing the wire of the invention for a lesser column strength, in certain embodiments, the UP can be configured to be at least 45% of the peak value of 304 stainless steel wire. When designing the wire of the invention for very high column strength, in certain embodiments, the UP can be configured to be at least 75% of the peak value of 304 stainless steel wire.

Further, while FIG. 3 shows the 3-point bend UP and Lower Plateau (LP) of the wire of the invention to be respectively greater than the 3-point bend UP and LP of the binary Nitinol alloy, the range of variance of the UP between the wire of the invention and binary Nitinol can be from approximately 45% to approximately 80%. Thus, when desiring a flexibility in the center of such range (so as to still have fair amount of corresponding column strength), the UP of the wire of the invention can be configured to be approximately 60% of the UP of Nitinol. When desiring flexibility more similar to that of Nitinol (with low amount of corresponding column strength), the UP of the wire of the invention can be configured to be 45% of the UP of Nitinol. When designing the wire of the invention for less flexibility than Nitinol (with high corresponding column strength), in certain embodiments, the UP can be configured to be at least 80% of the UP of Nitinol.

Figure 4:
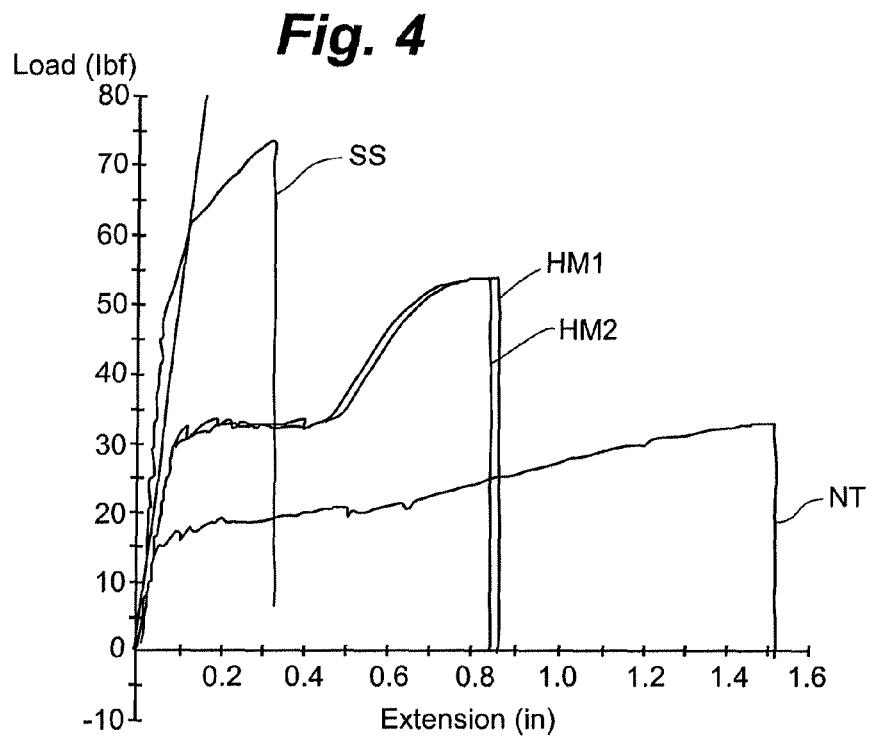
FIG. 4 is a graphical illustration of a stress—material failure relationship of the high-modulus superelastic alloy wire of the invention (before and after accelerated aging) as compared to stainless steel wire and binary Nitinol alloy wire.

FIG. 4 is a graphical illustration of a stress—material failure relationship of the high-modulus superelastic alloy wire of the invention (before and after accelerated aging) as compared to stainless steel wire (304 stainless steel) and binary Nitinol alloy wire, upon pull testing (via a pull until break test). Again, the stainless steel wire is referenced as line SS, the high-modulus superelastic alloy wire of the invention (both before and after accelerated aging) are referenced as lines HM1 and HM2, respectively, and the binary Nitinol alloy wire is referenced as line NT. Further, regarding the wire sizes of the specimens, all have substantially similar diameters, and with respect to the accelerated aging of the wire of the invention, the wire was aged at 75° C. for approximately 110 hours to represent a six-month shelf life.

With reference to FIG. 4, it generally confirms certain observations taken from FIG. 3; however, the column stiffness and strength of the specimens is more of the focus. In particular, the 304 stainless steel wire shows the least extension (poor flexibility) but can absorb the greatest amount of stress before failure (excellent column strength). By way of comparison, the binary Nitinol alloy wire shows the greatest extension (excellent flexibility) but absorbs the least amount of stress before failure (poor column strength). Looking to the high-modulus superelastic alloy wire specimens of the invention (before and after accelerated aging), they exhibited advantageous characteristics of each of the 304 stainless steel and binary Nitinol alloy wires. As shown, the wire of the invention exhibits higher extension properties than the stainless steel, and also exhibits higher column strength and stiffness than the binary Nitinol alloy wire.

It will be appreciated the embodiments of the present invention can take many forms. The true essence and spirit of these embodiments of the invention are defined in the appended claims, and it is not intended the embodiment of the invention presented herein should limit the scope thereof.

What is claimed is:

1. A wire used for one of medical or orthodontia purposes, comprising an elongated, flexible metal wire core at least partially formed of a trinary alloy, the trinary alloy consisting of Nickel, Titanium, and Cobalt, the trinary alloy formed principally of the Nickel and the Titanium with lesser additive of Cobalt, whereby the trinary alloy has both an upper plateau (UP) and a lower plateau (LP) from a 3-point bend test that are respectively greater than a UP and a LP from same 3-point bend test of binary Nitinol alloy with substantially similar diameter as the wire core, wherein extent by which the upper plateau (UP) and the lower plateau (LP) of the trinary alloy is greater than the upper plateau (UP) and the lower plateau (LP) of the binary Nitinol alloy is variable based on variance of weight components of the Nickel, the Titanium, and the Cobalt of the trinary alloy, wherein weight percentages of the Nickel and the Titanium are greater than 40% and the weight percentage of the Cobalt is less than or equal to 2%.

2. The wire of claim 1 wherein the UP of the trinary alloy is at least 45% greater than the UP of the binary Nitinol alloy.

3. The wire of claim 2 wherein the UP of the trinary alloy is in the range of between 45% and 80% greater than the UP of the binary Nitinol alloy.

4. The wire of claim 1 wherein the UP of the trinary alloy is at least 45% of peak value of 304 stainless steel alloy of substantially similar diameter of the wire core.

5. The wire of claim 4 wherein the UP of the trinary alloy is in the range between 45% and 75% of peak value of the stainless steel alloy.

6. The wire of claim 1 wherein the wire core is configured for use as part of a medical guidewire or stylet.

7. The wire of claim 1 wherein the wire core is configured for use as an orthodontia arch wire.

8. The wire of claim 1 wherein the weight percentage of the Cobalt is between 1.3% and 2%.

9. The wire of claim 1 wherein the elongated, flexible metal wire core is solely formed of the trinary alloy.

10. The wire of claim 9 wherein the trinary alloy exhibits a combination of column strength and kink resistance properties which fall between same properties of 304 stainless steel alloy of substantially similar diameter as the wire core and the binary Nitinol alloy.

11. A wire used for one of medical or orthodontia purposes, comprising an elongated, flexible metal wire core at least partially formed of a trinary alloy, the trinary alloy consisting of Nickel, Titanium, and Cobalt, the trinary alloy formed principally of the Nickel and the Titanium with lesser additive of Cobalt, whereby the trinary alloy has greater column strength and stiffness than binary Nitinol alloy of substantially similar diameter of the wire core, and the alloy having greater extension flexibility than 304 stainless steel alloy of substantially similar diameter of the wire core, wherein extent by which the trinary alloy has greater column strength and stiffness than the binary Nitinol alloy and extent by which the trinary alloy has greater extension flexibility than the 304 stainless steel alloy are variable based on variance of weight components of the Nickel, the Titanium, and the Cobalt of the trinary alloy, wherein weight percentages of the Nickel and the Titanium are reater than 40% and the weight percentage of the Cobalt is less than or equal to 2%.

12. The wire of claim 11 wherein the weight percentage of the Cobalt is between 1.3% and 2%.

13. The wire of claim 11 wherein the trinary alloy has both an upper plateau (UP) and a lower plateau (LP) from a 3-point bend test that are respectively greater than a UP and a LP from same 3-point bend test of the binary Nitinol alloy.

14. The wire of claim 13 wherein extent by which the upper plateau (UP) and the lower plateau (LP) of the trinary alloy is greater than the upper plateau (UP) and the lower plateau (LP) of the binary Nitinol alloy is variable based on variance of the weight components of the Nickel, the Titanium, and the Cobalt of the trinary alloy.

15. The wire of claim 14 wherein the UP of the trinary alloy is at least 45% greater than the UP of the binary Nitinol alloy.

16. The wire of claim 11 wherein the elongated, flexible metal wire core is solely formed of the trinary alloy.

17. The wire of claim 16 wherein the wire exhibits a favorable combination of column strength and kink resistance properties, wherein the column strength and kink resistance properties fall between same properties of the 304 stainless steel alloy and the binary Nitinol alloy.

18. A wire used for one of medical or orthodontia purposes, comprising an elongated, flexible metal wire core at least partially formed of a trinary alloy, the trinary alloy consisting of Nickel, Titanium, and Cobalt, the trinary alloy formed principally of the Nickel and the Titanium with lesser additive of Cobalt, whereby the trinary alloy exhibits a combination of column strength and kink resistance properties falling between same properties of 304 stainless steel alloy of substantially similar diameter of the wire core and of binary Nitinol alloy of substantially similar diameter of the wire core, wherein extent by which the trinary alloy has column strength and kink resistance properties falling closer to same properties of either the 304 stainless steel alloy or the binary Nitinol alloy are variable based on variance of weight components of the Nickel, the Titanium, and the Cobalt of the trinary alloy, wherein weight percentages of the Nickel and the Titanium are greater than 40% and the weight percentage of the Cobalt is less than or equal to to 2%.

19. The wire of claim 18 wherein the elongated, flexible metal wire core is solely formed of the trinary alloy.

20. The wire of claim 19 wherein the weight percentage of the Cobalt is between 1.3% and 2%.

21. A solid wire used for one of medical or orthodontia purposes, comprising an elongated, flexible metal solid wire core solely formed of a trinary alloy, the trinary alloy consisting of Nickel, Titanium, and Cobalt, the trinary alloy formed principally of the Nickel and the Titanium with lesser additive of Cobalt, whereby the trinary alloy has both an upper plateau (UP) and a lower plateau (LP) from a 3-point bend test that are respectively greater than a UP and a LP from same 3-point bend test of binary Nitinol alloy with substantially similar diameter as the solid wire core, wherein extent by which the upper plateau (UP) and the lower plateau (LP) of the trinary alloy is greater than the upper plateau (UP) and the lower plateau (LP) of the binary Nitinol alloy is variable based on variance of weight components of the Nickel, the Titanium, and the Cobalt of the trinary alloy present in the wire core, and wherein weight percentages of the Nickel and the Titanium are greater than 40% and the weight percentage of the Cobalt is less than or equal to 2%.

22. The solid wire of claim 21 wherein the weight percentage of the Cobalt is between 1.1% and 2%.

23. The solid wire of claim 21 wherein the UP of the trinary alloy is at least 45% greater than the UP of the binary Nitinol 24. The solid wire of claim 23 wherein the UP of the trinary alloy is in the range of between 45% and 80% greater than the UP of the binary Nitinol alloy.

25. The solid wire of claim 21 wherein the UP of the trinary alloy is at least 45% of peak value of 304 stainless steel alloy of substantially similar diameter of the wire core.

26. The solid wire of claim 25 wherein the UP of the trinary alloy is in the range between 45% and 75% of peak value of the stainless steel alloy.

27. The solid wire of claim 21 wherein the wire core is configured for use as part of a medical guidewire or stylet.

28. The solid wire of claim 21 wherein the wire core is configured for use as an orthodontia arch wire.

29. The solid wire of claim 21 wherein the trinary alloy exhibits a combination of column strength and kink resistance properties which fall between same properties of 304 stainless steel alloy of substantially similar diameter as the wire core and the binary Nitinol alloy.

30. A solid wire used for one of medical or orthodontia purposes, comprising an elongated, flexible metal wire core solely formed of a trinary alloy, the trinary alloy consisting of Nickel, Titanium, and Cobalt, the trinary alloy formed principally of the Nickel and the Titanium with lesser additive of Cobalt, whereby the trinary alloy has greater column strength and stiffness than binary Nitinol alloy of substantially similar diameter of the wire core, and the alloy having greater extension flexibility than 304 stainless steel alloy of substantially similar diameter of the wire core, wherein extent by which the trinary alloy has greater column strength and stiffness than the binary Nitinol alloy and extent by which the trinary alloy has greater extension flexibility than the 304 stainless steel alloy are variable based on variance of the weight components of the Nickel, the Titanium, and the Cobalt of the trinary alloy present in the wire core, and wherein weight percentages of the Nickel and the Titanium are greater than 40% and the weight percentage of the Cobalt is less than or equal to 2%.

31. The solid wire of claim 30 wherein the weight percentage of the Cobalt is between 1.3% and 2%.

32. The solid wire of claim 30 wherein the tri nary alloy has both an upper plateau (UP) and a lower plateau (LP) from a 3-point bend test that are respectively greater than a UP and a LP from same 3-point bend test of the binary Nitinol alloy.

33. The solid wire of claim 32 wherein extent by which the upper plateau (UP) and the lower plateau (LP) of the trinary alloy is greater than the upper plateau (UP) and the lower plateau (LP) of the binary Nitinol alloy is variable based on variance of the weight components of the Nickel, the Titanium, and the Cobalt of the trinary alloy.

34. The solid wire of claim 33 wherein the UP of the trinary alloy is at least 45% greater than the UP of the binary Nitinol 35. The solid wire of claim 30 wherein the wire exhibits a favorable combination of column strength and kink resistance properties, wherein the column strength and kink resistance properties fall between same properties of the 304 stainless steel alloy and the binary Nitinol alloy.

36. A solid wire used for one of medical or orthodontia purposes, comprising an elongated, flexible metal wire core soley formed of a trinary alloy, the trinary alloy consisting of Nickel, Titanium, and Cobalt, the trinary alloy formed principally of the Nickel and the Titanium with lesser additive of Cobalt, whereby the trinary alloy exhibits a combination of column strength and kink resistance properties falling between same properties of 304 stainless steel alloy of substantially similar diameter of the wire core and of binary Nitinol alloy of substantially similar diameter of the wire core, wherein extent by which the trinary alloy has column strength and kink resistance properties falling closer to same properties of either the 304 stainless steel alloy or the binary Nitinol alloy are variable based on variance of weight components of the Nickel, the Titanium, and the Cobalt of the trinary alloy present in the wire core, and wherein weight percentages of the Nickel and the Titanium are greater than 40% and the weight percentage of the Cobalt is less than or equal to 2%.

37. The solid ire of claim 36 wherein the weight percentage of the Cobalt is between 1.3% and 2%.

* * * * *